(12) United States Patent
Fukuma et al.

(10) Patent No.: US 7,837,328 B2
(45) Date of Patent: Nov. 23, 2010

(54) OPTICAL IMAGE-MEASURING DEVICE

(75) Inventors: Yasufumi Fukuma, Tokyo (JP); Hisashi Tsukada, Tokyo (JP); Tsutomu Kikawa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 11/621,779

(22) Filed: Jan. 10, 2007

(65) Prior Publication Data

US 2007/0159597 A1  Jul. 12, 2007

(30) Foreign Application Priority Data

Jan. 11, 2006  (JP) .............................. 2006-003881

(51) Int. Cl.
*A61B 3/14* (2006.01)
(52) U.S. Cl. ..................... 351/206; 351/205; 351/200
(58) Field of Classification Search ................. 351/212, 351/205, 206
See application file for complete search history.

(56) References Cited

U.S. PATENT DOCUMENTS

| | | | |
|---|---|---|---|
| 4,412,728 A * | 11/1983 | Sakane et al. ................ | 351/206 |
| 5,501,226 A * | 3/1996 | Petersen et al. ............. | 600/504 |
| 5,537,162 A * | 7/1996 | Hellmuth et al. ............ | 351/206 |
| 5,644,642 A * | 7/1997 | Kirschbaum ................ | 382/103 |
| 5,894,337 A * | 4/1999 | Okinishi et al. ............. | 351/205 |
| 5,975,697 A * | 11/1999 | Podoleanu et al. .......... | 351/206 |
| 5,975,699 A | 11/1999 | Hellmuth | |
| 6,004,314 A | 12/1999 | Wei et al. | |
| 6,198,540 B1 | 3/2001 | Ueda et al. | |
| 2005/0020925 A1 | 1/2005 | Kleen et al. | |
| 2005/0157259 A1* | 7/2005 | Akita et al. .................. | 351/206 |
| 2006/0187462 A1 | 8/2006 | Srinivasan et al. | |
| 2006/0276709 A1 | 12/2006 | Khamene et al. | |

FOREIGN PATENT DOCUMENTS

| | | |
|---|---|---|
| DE | 10323217 | 12/2004 |
| EP | 0697611 | 2/1996 |
| EP | 0956810 | 11/1999 |
| EP | 1 769 732 A2 | 4/2007 |
| JP | 2003-000543 | 1/2003 |
| JP | 2004-350849 | 12/2004 |
| JP | 2005-241464 | 9/2005 |

OTHER PUBLICATIONS

European Search Report.
European Office Action dated Dec. 2, 2009 issued in European Patent Application No. 08 000 290.2.
European Office Action dated Sep. 28, 2008 issued in European Patent Application No. 07 000 290.2.

* cited by examiner

*Primary Examiner*—Joseph Martinez
*Assistant Examiner*—James R Greece
(74) *Attorney, Agent, or Firm*—Edwards Angell Palmer & Dodge LLP

(57) ABSTRACT

Light is split into a signal light LS directed toward the fundus oculi Ef and a reference light LR directed toward a reference mirror 174, and interference light LC generated by superimposing the signal light LS passing through the fundus oculi Ef and the reference light LR passing through the reference mirror 174 using a spectrometer 180 is detected to form tomographic images. A reference mirror drive mechanism 243 shifts the reference mirror 174 toward the optical path direction of the reference light LR and an information storage part 225 storing the reference mirror 174 position information based on previous tomographic images. The controlling part 210 controls the reference mirror drive mechanism 243 so that the reference mirror 174 shifts into a position based on reference mirror position information stored in the information storage part 225.

4 Claims, 11 Drawing Sheets

FIG.6
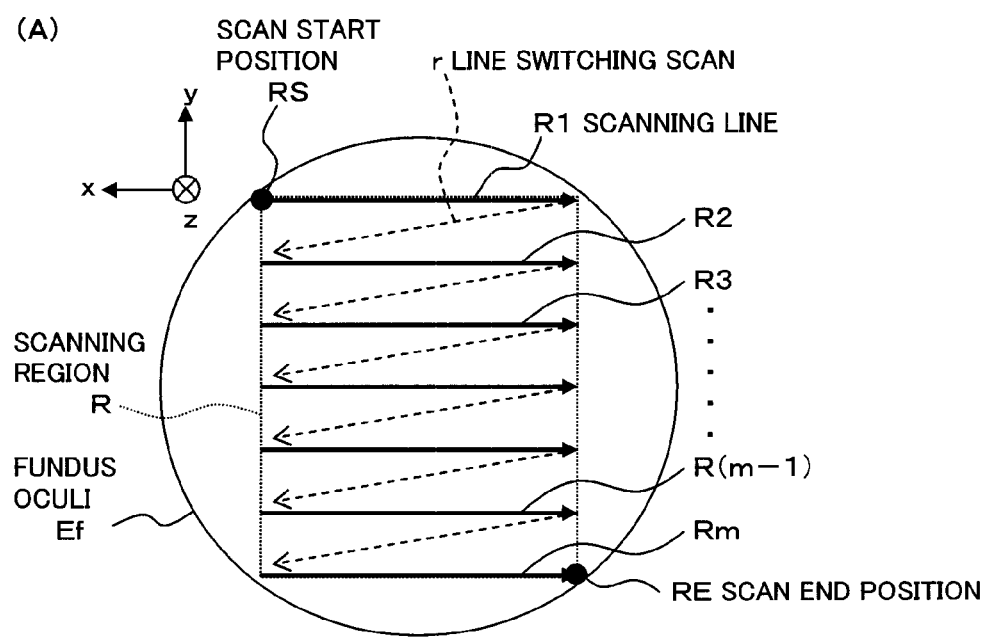
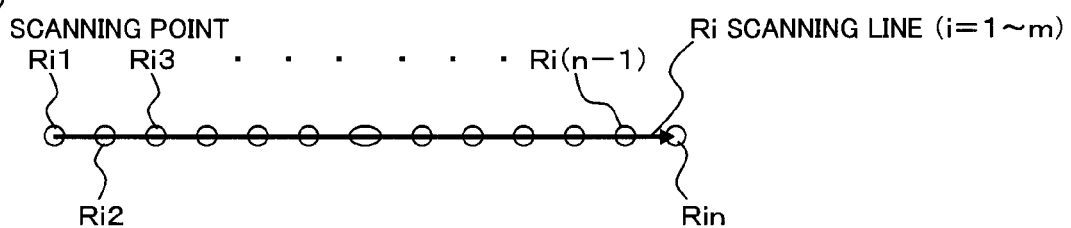

OPTICAL IMAGE-MEASURING DEVICE

BACKGROUND OF THE INVENTION

1. Field of the Invention

This invention relates to an optical image-measuring device for observing the surface of the fundus oculi of an eye to be examined as well as deep layer tissue formation.

2. Description of the Related Art

As a device for observing the fundus oculi of an eye to be examined (a fundus observation device), a fundus camera has been widely used, conventionally. FIG. 10 shows one example of the appearance of a conventional fundus camera in general, and FIG. 11 shows one example of an optical system composition to be internally accommodated therein (e.g. JP Patent laid-open No. 2004-350849). Furthermore, "observation" is intended to include at least a case in which produced fundus images are observed (observations with the naked eye may be included).

First, referring to FIG. 10, an explanation is made regarding the appearance of a conventional fundus camera 1000. This fundus camera is provided with a platform 3 mounted on a base 2 slidably in the front and rear, right and left (horizontal direction) directions. On this platform 3, an operation panel 3a and a joystick 4 are installed for an examiner to conduct various operations.

The examiner may place the platform 3 on the base 2 to be moved 3-dimensionally by operating the joystick 4. On the top of the joystick 4, an operation button 4a is installed to be pressed down to form fundus oculi images.

On the base 2, a post 5 is installed standing upwards. On the post 5, a jaw rest 6 where the jaw of a patient is to be rested and an external fixation lamp 7 as a light source for fixing an eye to be examined E are provided.

On the platform 3, a main body part 8 is installed to accommodate various optical systems or control systems of the fundus camera 1000. Furthermore, the control system may be installed inside the base 2 or the platform, etc., or in an external device such as a computer, etc. connected to the fundus camera 1000.

On the side of the eye to be examined E of the main body part 8 (the left side of the page in FIG. 10), an objective lens part 8a disposed opposite the eye to be examined E is installed. Also, on the examiner's side of the main body part 8 (the right side of the page in FIG. 9), an objective lens part 8b for observing the fundus oculi of the eye to be examined E with the naked is installed.

Furthermore, connected to the main body part 8 is a still camera 9 for producing a still image of a fundus oculi of the eye to be examined E and an imaging device 10 such as a TV camera, etc. for producing still images or moving images of a fundus oculi. The still camera 9 and the imaging device 10 are formed removably with respect to the main body part 8.

As a still camera 9, in accordance with various conditions such as the purpose of an examination or the saving method of obtained images, etc., a digital camera equipped with imaging elements such as CCD (Charge Coupled Device) or CMOS (Complementary Metal Oxide Semiconductor), a film camera, an instant camera, etc. may interchangeably be used when it is appropriate. The main body part 8 is equipped with a mounting part 8c for interchangeably mounting such a still camera 9.

If the still camera 9 or the imaging device 10 is for taking digital images, the image data of the produced fundus image may be sent to a device such as a computer, etc. connected to the fundus camera 1000 and be observed as a fundus image by being displayed on the display. Also, the image data in an image storing device connected to the fundus camera 1000 can be sent to compile a database and be used as electronic data for creating medical charts, etc.

Furthermore, on the examiner's side of the main body part 8, a touch panel monitor 11 is installed. On this touch panel monitor 11, fundus images of the eye to be examined E created based on the picture signals output from the still camera 9 (a digital method thereof) or the imaging device 10 are displayed. Moreover, on the touch panel monitor 11, the xy coordinate system with the center of the screen as the origin is displayed overlapped with a fundus image. When the screen is touched by the examiner, the coordinate value corresponding to the touched position is displayed.

Next, referring to FIG. 11, a composition of an optical system of the fundus camera 1000 is described. The fundus camera 1000 is provided with an illuminating optical system 100 to light the fundus oculi Ef of an eye to be examined E, an imaging optical system 120 to guide the fundus reflection light of the illumination light to the eyepiece part 8b, a still camera 9, and an imaging device 10.

The illuminating optical system 100 comprises: an observation light source 101, a condenser lens 102, an imaging light source 103, a condenser lens 104, an exciter filter 105 and 106, a ring transparent plate 107, a mirror 108, a liquid crystal display (LCD) 109, an illumination diaphragm 110, a relay lens 111, an aperture mirror 112, and an objective lens 113.

The observation light source 101 consists of a halogen lamp, etc. and emits fixed light (continuous light) for observing the fundus. The condenser lens 102 is an optical element that converges the fixed light (observation illumination light) emitted by the observation light source 101 and substantially evenly irradiates the observation illumination light to the fundus oculi.

The imaging light source 103 consists of a xenon lamp, etc. to be flashed when producing fundus oculi Ef images. The condenser lens 104 is an optical element that converges the flash light (imaging illumination light) emitted by the imaging light source 103 and irradiates the fundus oculi Ef evenly with the imaging illumination light.

The exciter filters 105 and 106 are the filters to be used when fluorography of ocular fundus images of a fundus oculi Ef takes a place. The exciter filters 105 and 106 respectively can be inserted and/or removed on the optical path by a drive mechanism such as a solenoid, etc. The exciter filter 105 is disposed on the optical path in the event of FAG (fluorescein angiography). Whereas, the exciter filter 106 is disposed on the optical path in the event of ICG (indocyanine green angiography). Furthermore, when color images are being obtained, both exciter filters 105 and 106 are retracted from the optical path.

The ring transparent plate 107 is disposed in a conjugating location with a pupil of the eye to be examined E, and is equipped with a ring transparent part 107a taking an optical axis of the illuminating optical system 100 as a center. The mirror 108 reflects the illumination light emitted by the observation light source 101 or by the imaging light source 103 in the direction of the optical axis of the imaging optical system 120. The LCD 109 displays a fixation target (not illustrated) for fixing the eye to be examined E.

The illumination diaphragm 110 is a diaphragm member to shut out a part of the illumination light for flare prevention, etc. This illumination diaphragm 110 is composed movably in the light axial direction of the illuminating optical system 100, and is thus capable of changing the illuminating region of the fundus oculi Ef.

The aperture mirror 112 is an optical element to combine an optical axis of the illuminating optical system 100 and an optical axis of the imaging optical system 120. In the center region of the aperture mirror 112 an aperture part 112a is opened. The light axis of the illuminating optical system 100 and the light axis of the imaging optical system 120 are to be crossed at a substantially central location of this aperture part 112a. The objective lens 113 is installed in the objective lens part 8a of the main body part 8.

The illuminating optical system 100 having such a composition illuminates a fundus oculi Ef in the following manner. First, the observation illumination light is output when the observation light source 101 is lit during fundus observation. This observation illumination light irradiates the ring transparent plate 107 through the condenser lenses 102 and 104. The exciter filters 105 and 106 are removed from the optical path. The light passed through the ring transparent part 107a of the ring transparent plate 107 is reflected by the mirror 108 and is reflected along the optical axial direction of the imaging optical system 120 due to the aperture mirror 112 through the LCD 109, the illumination diaphragm 110 and the relay lens 111. The observing illumination light reflected by the aperture mirror 112 advances in the optical axial direction of the imaging optical system 120 and is converged by the objective lens 113, to be made incident onto the eye to be examined E, and illuminates the fundus oculi Ef.

Then, the ring transparent plate 107 is disposed in a conjugating location with the pupil of the eye to be examined E, and on the pupil a ring shaped image of the entering observation illumination light is formed. The fundus reflection light of the entered observation illumination light is to be emitted from the eye to be examined E through a central dark part of the ring image on the pupil. As described, it is to protect the effect of observing illumination light entering the eye to be examined E with respect to the fundus reflection light of the observing illumination light.

On the other hand, when imaging the fundus oculi Ef, flush light is emitted from the imaging light source 103 and the imaging illumination light is irradiated onto the fundus oculi Ef through the same path. In the event of photofluographing, either the exciter filter 105 or the exciter filter 106 is disposed selectively on the optical path depending on whether FAG imaging or ICG imaging is required.

Whereas, imaging optical system 120 comprises: an objective lens 113, an aperture mirror 112 (an aperture part 112a thereof), an imaging diaphragm 121, a barrier filter 122 and 123, a variable magnifying lens 124, a relay lens 125, an imaging lens 126, a quick return mirror 127 and an imaging media 9a. Herein, the imaging media 9a is an arbitrary imaging media (image pick-up elements such as CCD, camera film, instant film, etc.) used for a still camera 9.

The fundus reflection light of the illumination light emitted through the central dart part of the ring shaped image center formed on the pupil from the eye to be examined E, enters the imaging diaphragm 121 through the aperture part 112a of the aperture mirror 112. The aperture mirror 112 reflects cornea reflection light of the illumination light and acts so as not to mix the cornea reflection light into the fundus reflection light made incident onto the imaging diaphragm 121. As a result, the generation of flare on the observation images and/or produced images is prevented.

The imaging diaphragm 121 is a plate shaped member at which plural circular light transparent parts of different sizes are formed. The plural light transparent parts constitute different diaphragms with different diaphragm values (F value), and are to be disposed alternatively on the optical path by a drive mechanism not illustrated herein.

The barrier filters 122 and 123 can be inserted and/or removed on the optical path by a drive mechanism such as a solenoid, etc. In the event of FAG imaging, the barrier filter 122 is disposed on the optical path while in the event of ICG imaging the barrier filter 123 is inserted onto the optical path. Furthermore, when producing color images the barrier filters 122 and 123 are to be retracted from the optical path.

The variable magnifying lens 124 is to be movable in the light axial direction of the imaging optical system 120 by a drive mechanism not illustrated herein. This makes it possible to change the magnifying ratio of an observation and the magnifying ratio in imaging, and to focus images of a fundus oculi. The imaging lens 126 is a lens to form an image of the fundus reflection light from an eye to be examined E on the imaging media 9a.

The quick return mirror 127 is disposed rotatably around a rotary shaft 127a by a drive mechanism not illustrated herein. In the event of imaging a fundus oculi Ef with the still camera 9, the fundus reflection light is supposed to be guided to the imaging media 9a by springing up the quick return mirror 127 that is obliquely mounted on the optical path. Whereas, in the event of imaging a fundus oculi with an imaging device 10 or of observing the fundus oculi with the naked eye of the examiner, the quick return mirror 127 is to be obliquely mounted on the optical path to upwardly reflect the fundus reflection light.

The imaging optical system 120 is further provided with a field lens (eye vision lens) 128 for guiding the fundus reflection light reflected by the quick return mirror 127, a switching mirror 129, an eyepiece 130, a relay lens 131, a reflection mirror 132, an imaging lens 133 and an image pick up element 10a. The image pick up element 10a is an image pick up element such as CCD, etc. installed internally in the imaging device 10. On the touch panel monitor 11 a fundus oculi image Ef' produced by the image pick up element 10a is be displayed.

The switching mirror 129 is to be rotatable around the rotary shaft 129a as well as the quick return mirror 127. This switching mirror 129 is obliquely disposed on the optical path during observation with the naked eye and guides reflected light on the fundus oculi to the eyepiece 130.

Also, when a fundus image is formed by the imaging device 10, the switching mirror 129 is retracted from the optical path, and the fundus reflection light is guided toward an image pick-up element 10a. In this case, the fundus reflection light is directed toward a relay lens 131, is reflected by the mirror 132, and is formed on the image pick-up element 10a by the imaging lens 133.

Such a fundus camera 1000 is a fundus observation apparatus to be used for observing the state of the surface of a fundus oculi Ef, that is, the retina. In other words, a fundus camera 1000 is a fundus observation apparatus to obtain a 2-dimensional fundus oculi image when it sees the fundus oculi Ef from the corneal direction onto the eye to be examined E. On the other hand, in the deep layer of retina tissues such as where the choroidea or sclera exist, technology for observing these deep layer tissues has been desired, but, in recent years, devices for observing these deep layer tissues have been practically implemented (e.g. JP Patent laid-open No. 2003-00543, JP Patent laid-open No. 2005-241464).

The optical image-measuring device disclosed in JP Patent laid-open No. 2003-00543 and JP Patent laid-open No. 2005-241464 are devices to which so called OCT (Optical Coherence Tomography) technology is applied. With such optical image-measuring devices, low coherence light is split into two, one of which (signal light) is guided to a fundus oculi and the other one (reference light) is guided to a given reference object, while at the same time this is a device to form tomographic images of the surface and the deep layer tissue of a fundus oculi, and to form the 3-dimensional image from the tomographic images, by detecting and analyzing the interference light obtained by overlaying the signal light that has passed through the fundus oculi and the reference light that has been reflected by the reference object.

When measuring the fundus image using an optical image-measuring device, or the like, the position of the reference object must be adjusted to the eye to be examined before actually measurement. That is, the image must be measured with the reference object located in an appropriate position for said eye to be examined considering that the characteristics each patient differ individually in eyeball length, and the eye position when the chin is placed on the rest 6.

When observing improvement in fundus oculi after surgery or treatment, where the fundus oculi is repeatedly observed for said eye to be examined, the surgical area or treated area is observed repeatedly and the position of the reference object must be adjusted each time. This increases the burden on the examinee subject to examination due to longer examination time as well as the burden on the examiner due to the troublesome task of positioning the reference object, which has remained a problem.

Furthermore, on the type of optical image-measuring device described in JP Patent laid-open No. 2003-00543, which scans a signal light, when repeatedly observing the surgical area, the scanning positions of the signal light (scanning start position, scanning end position, scan interval) must be set each time. This increases the examination time and the task of setting the scanning positions, which has remained a problem.

This invention is designed to solve these problems, saving long examination time when repeatedly observing the fundus oculi of the same eye to be examined, and the purpose is to provide an optical image-measuring device that can reduce some troublesome tasks.

SUMMARY OF THE INVENTION

In order to achieve the above purpose, the first aspect of the present invention is constructed as follows: An optical image-measuring device having: a light source; an interference optical generating means splitting light that is output from said light source into a signal light directed toward a fundus oculi of an eye to be examined and a reference light directed toward a reference object, and generating an interference light by superimposing said signal light passing through said fundus oculi and said reference light passing through said reference object; and a detecting means detecting said interference light that is generated, and forming tomographic images of said fundus oculi based on the detection results by said detecting means, wherein the optical image-measuring device comprises a storing means for storing position information indicating the position of said reference object based on previously formed said tomographic images; and a driving means for shifting said reference object toward the optical path direction of said reference light based on said reference object position information related to said eye to be examined, which is stored in said storing means before said light source outputs light.

The second aspect of the present invention is constructed as follows: An optical image-measuring device having: a light source; an interference optical generating means splitting light output from said light source into a signal light directed toward a fundus oculi of an eye to be examined and a reference light directed toward a reference object, and generating an interference light by superimposing said signal light passing through said fundus oculi and said reference light passing through said reference object; and a detecting means detecting said interference light being generated, and forming tomographic images of said fundus oculi based on the detection results by said detecting means, wherein the optical image-measuring device comprises a storing means that stores scanning position information that indicates the scanning position of said signal light at the time said tomographic images were formed; and a scanning means that scans said signal light directed toward said fundus oculi of an eye to be examined based on said scanning position information related to said eye to be examined that is stored in said storing means.

Effects of the Invention

The optical image-measuring device related to the first aspect of the present invention has a driving means that shifts the reference object toward the optical path direction of the reference light, and a storing means that stores the position information of the reference object based on previously formed tomographic images of the fundus oculi. The driving means is configured to shift the reference object to positions based on position information of the reference object, which is stored in the storing means, related to said eye to be examined before the light source outputs light.

Consequently, when repeatedly observing the fundus oculi of the same eye to be examined, the position of the reference object is automatically set based on the position information of the reference object based on previously formed tomographic images, which saves on long examination time. Furthermore, manually setting is no longer necessary for reference object positioning, which reduces troublesome tasks before beginning the examination.

Furthermore, the optical image-measuring device related to the second aspect of the present invention has a scanning means that scans the signal light directed at the fundus oculi of an eye to be examined and a storing means that stores the scanning position information of the signal light from previously formed tomographic images. The scanning means is configured to scan the signal light based on the scanning position information related to said eye to be examined being stored in the storing means.

Thus, when repeatedly observing the fundus oculi of the same eye to be examined, the signal light is scanned based on the scanning position information of the signal light from previously formed tomographic images and the setting task for scanning position of the signal light is no longer necessary, which saves on long examination time. Furthermore, the setting task, which had formerly been done manually, is no longer necessary for the scanning position, thereby reducing troublesome tasks before beginning an examination.

BRIEF DESCRIPTION OF THE DRAWINGS

FIG. 6 is a schematic diagram representing one example of scanning features of signal light in a favorable embodiment of the fundus observation device configured to include the optical image-measuring device related to the present invention. FIG. 6(A) represents one example of the scanning features of signal light when a fundus oculi is seen from the incident side of the signal light with respect to an eye to be examined. In addition, FIG. 6 (B) represents one example of arrangement features of scanning points of each scanning line.

DETAILED DESCRIPTION OF THE REFERENCE EMBODIMENT

Figure 10:
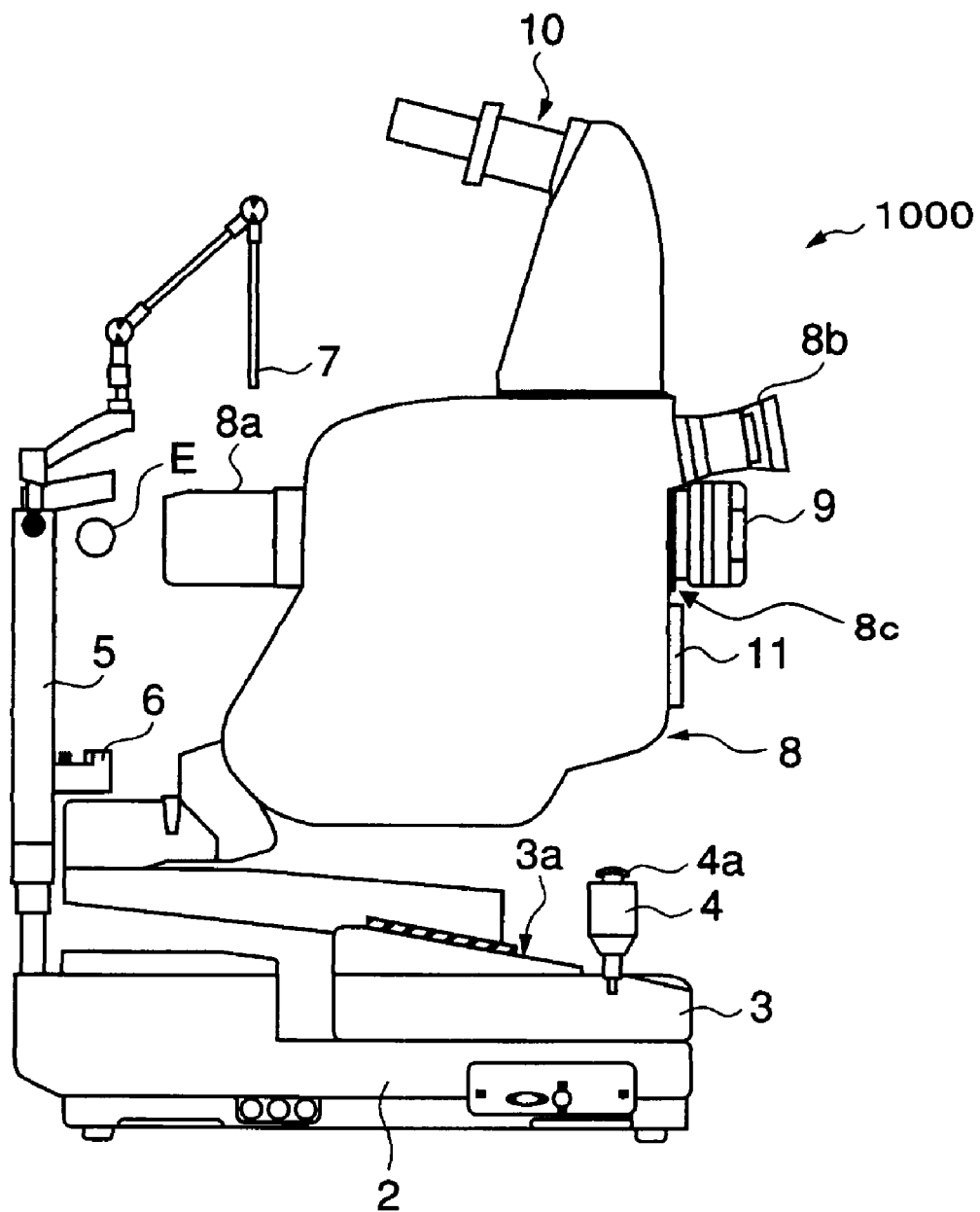
FIG. 10 is a schematic side view representing an appearance constitution of a conventional fundus observation device (fundus camera).
Figure 11:
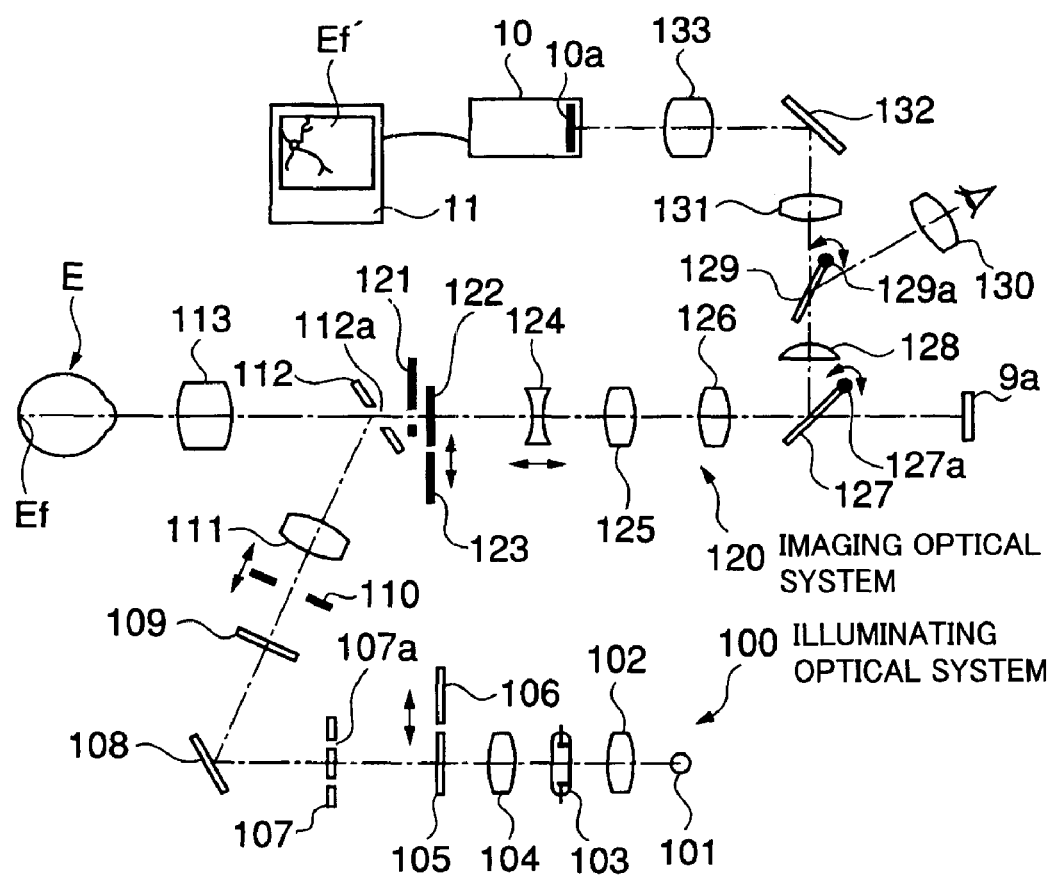
FIG. 11 is a schematic diagram representing one example of an internal constitution (an optical system constitution) of a conventional fundus observation device (fundus camera).

One example of embodiments of an optical image-measuring device related to the present invention is described in detail referring to figures. Furthermore, for compositional parts that are the same as conventional ones, the same numeric symbols used in FIG. 10 and FIG. 11 are used.

Figure 1:
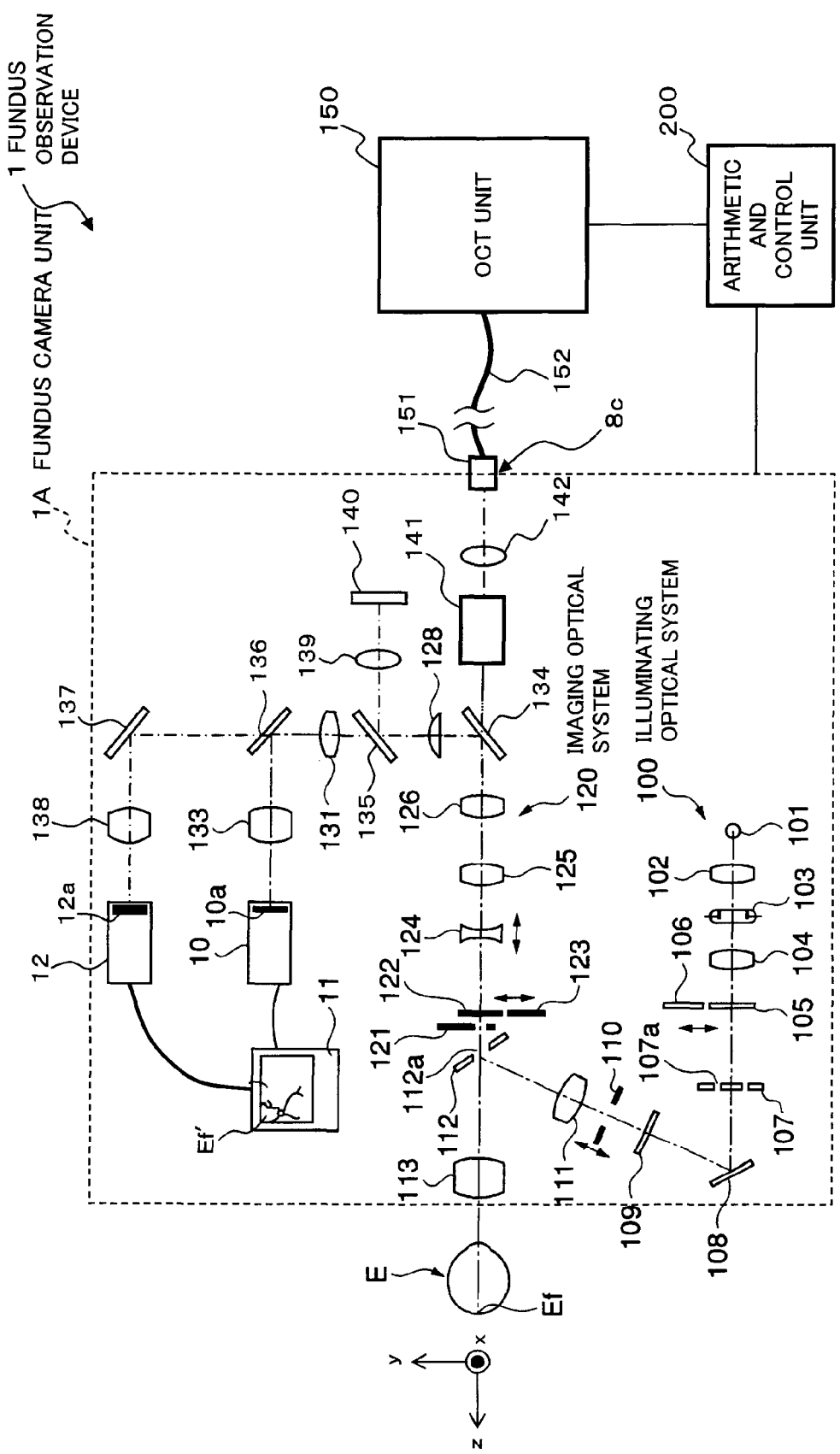
FIG. 1 is a schematic diagram that shows the preferred embodiment of an entire configuration of a fundus observation device configured to include the optical image-measuring device related to the present invention.
Figure 2:
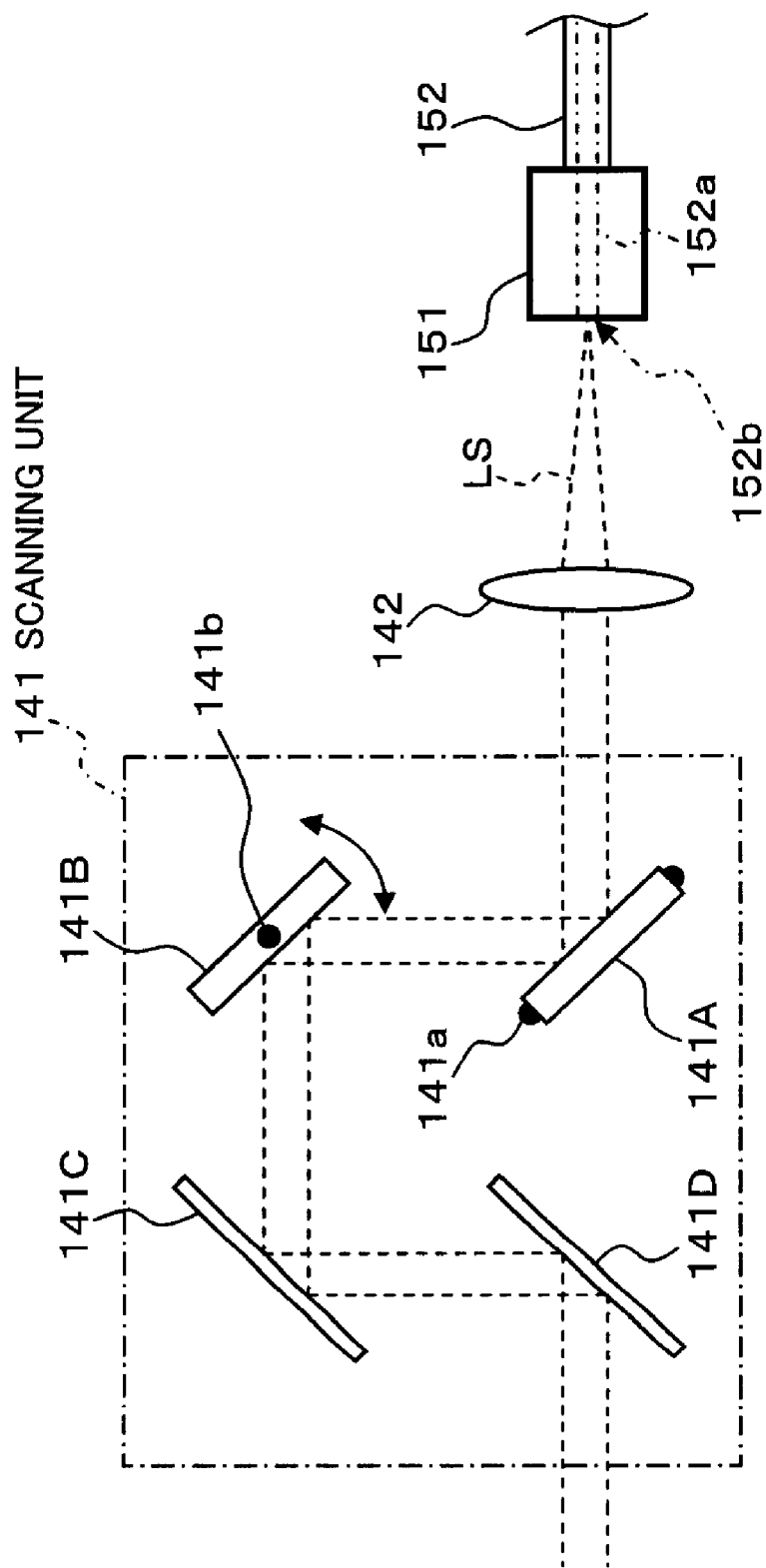
FIG. 2 is a schematic diagram representing one compositional example of a scanning unit installed in a fundus camera unit in a favorable embodiment of the fundus observation device configured to include the optical image-measuring device related to the present invention.
Figure 3:
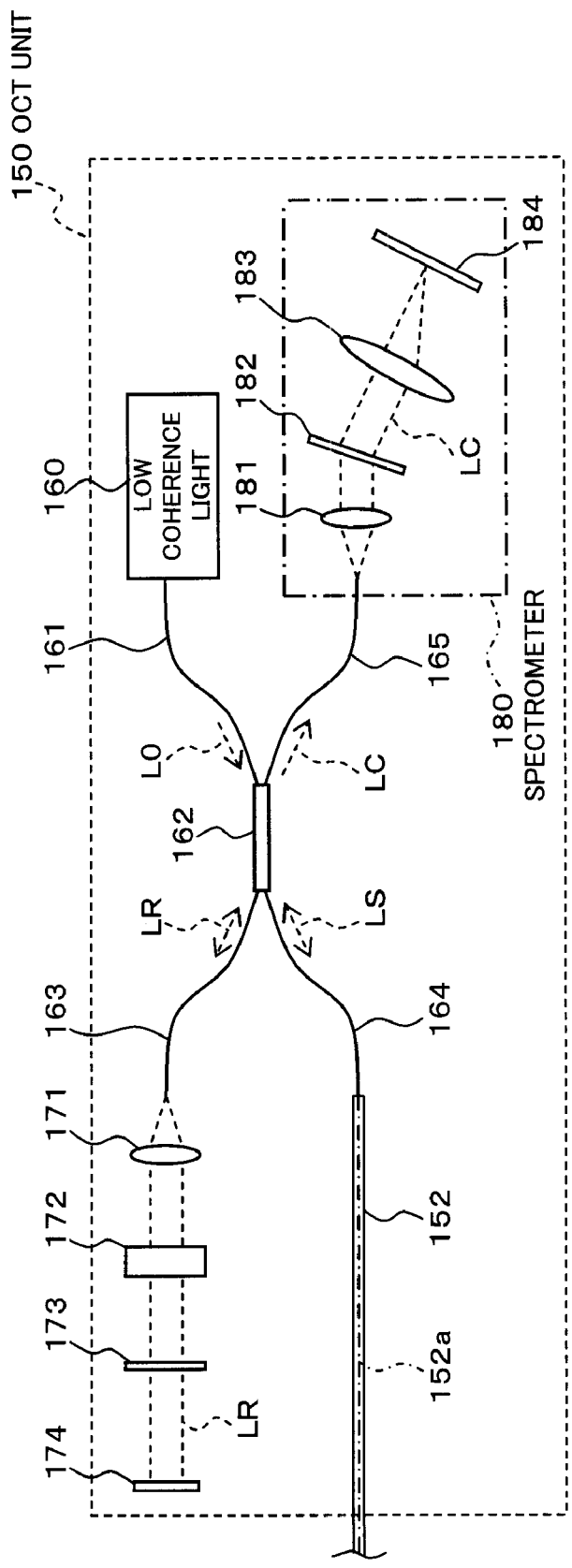
FIG. 3 is a schematic diagram representing one compositional example of an OCT unit in a favorable embodiment of the fundus observation device configured to include the optical image-measuring device related to the present invention.
Figure 4:
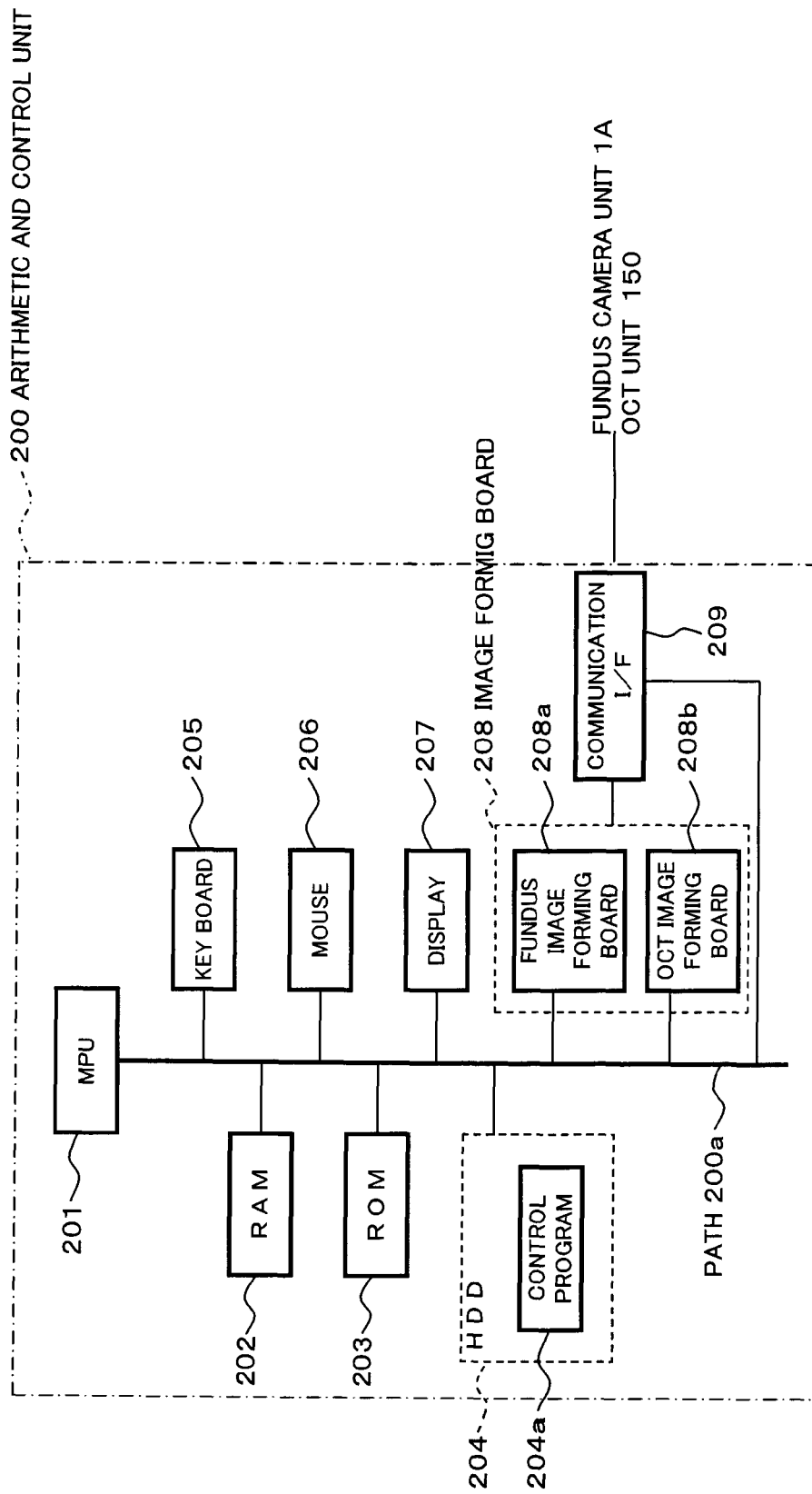
FIG. 4 is a schematic block diagram representing one example of hardware configurations of an arithmetic and control unit in a favorable embodiment of the fundus observation device configured to include the optical image-measuring device related to the present invention.
Figure 5:
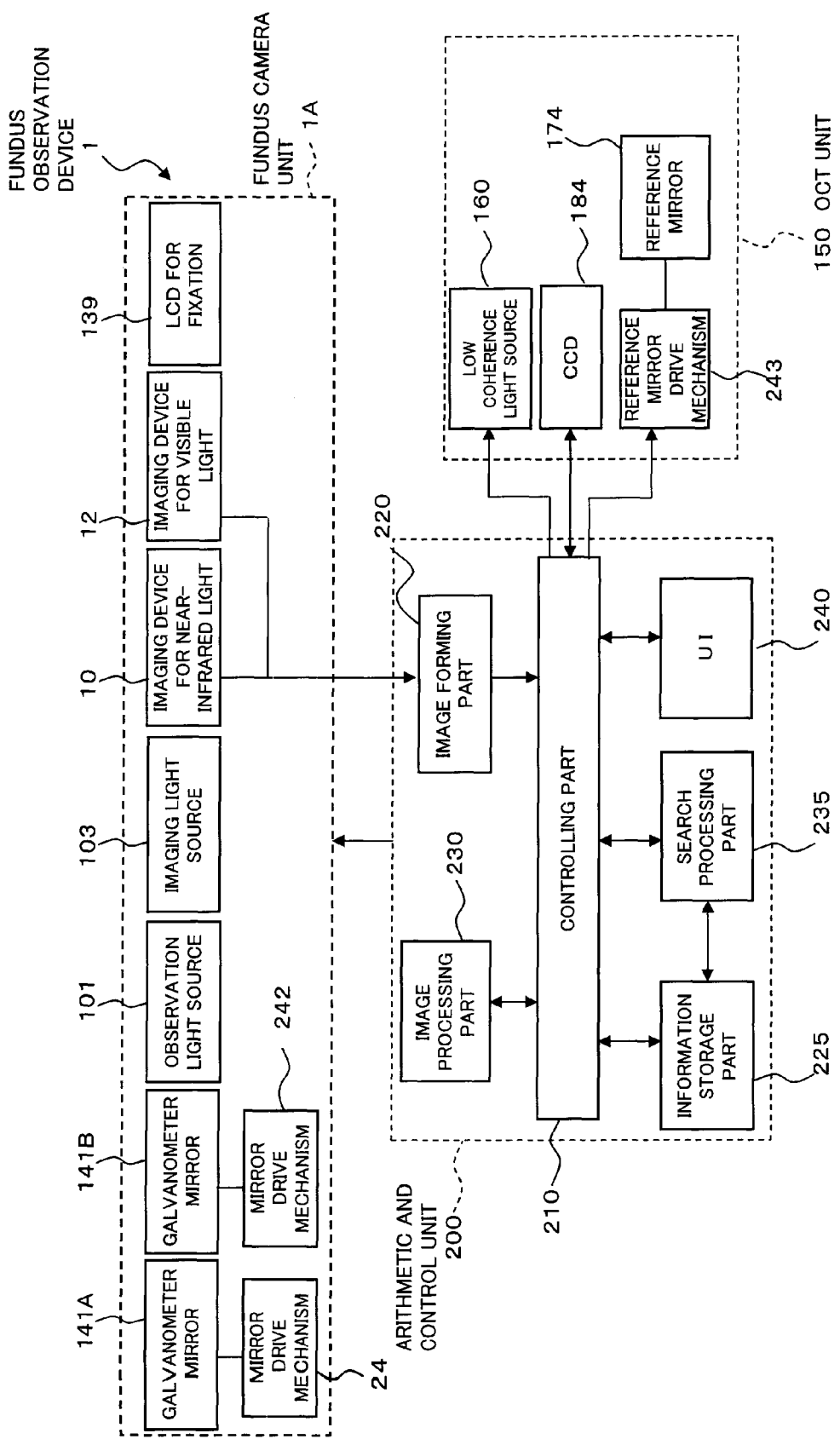
FIG. 5 is a schematic block diagram representing one compositional example of a control system in a favorable embodiment of the fundus observation device configured to include the optical image-measuring device related to the present invention.

First, by referring to FIGS. 1 through 5, the composition of the present Embodiment of the optical image-measuring device related to the present invention is described. FIG. 1 shows the entire constitution of the fundus observation device 1 having both functions of an optical image-measuring device and a fundus camera. FIG. 2 shows a composition of a scanning unit 141 in a fundus camera unit 1A. FIG. 3 shows a composition of an OCT unit 150. FIG. 4 shows a hardware configuration of an arithmetic and control unit 200. FIG. 5 shows a configuration of a control system of the fundus observation device 1.

As shown in FIG. 1, the fundus observation device 1 a component of a fundus camera unit 1A that functions as a fundus camera, an OCT unit 150 accommodating the optical system of an optical image-measuring device (OCT device), and an arithmetic and control unit 200 that executes various control processes, etc.

The OCT unit 150 is a component of one example of the "optical image-measuring device" with the arithmetic and control unit 200. Further, this "optical image-measuring device" also includes each optical element through the signal light such as a scan unit 141 provided in the fundus camera unit 1A, etc.

To the OCT unit 150, one end of a connection line 152 is attached. To the other end of this connection line 152, a connector part 151 is attached. This connector part 151 is attached to a mounting part 8c shown in FIG. 10. Furthermore, a conductive optical fiber runs through the inside of the connection line 152. The OCT unit 150 and the fundus camera unit 1A are optically connected through the connection line 152. The composition details of the OCT unit 150 are to be described later referring to FIG. 3.

Constitution of Fundus Camera Unit

Figure 9:
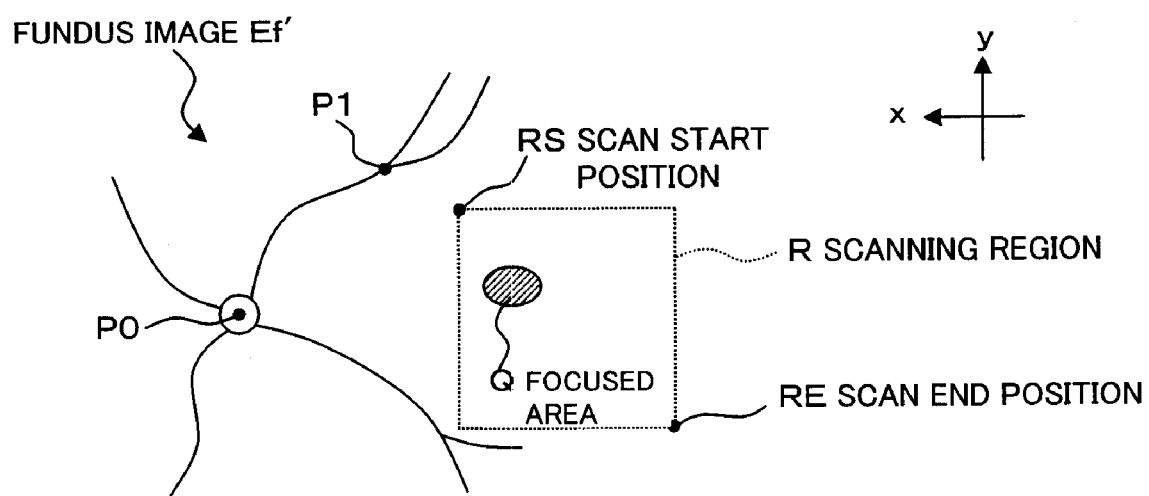
FIG. 9 is a schematic explanatory diagram explaining a modified example of the preferred embodiment of the fundus observation device configured to include the optical image-measuring device related to the present invention.

The fundus camera unit 1A has substantially the same appearance as the conventional fundus camera 1000 shown in FIG. 9. Furthermore, as in the conventional optical system shown in FIG. 10, the fundus camera unit 1A is provided with an illuminating optical system 100 to light a fundus oculi Ef of an eye to be examined E, and an imaging optical system 120 for guiding the fundus reflection light of the illumination light to an eyepiece 8b, an imaging device 10, and an OCT unit 150.

In addition, although the details are to be described later, an imaging device 10 in an imaging optical system 120 of the present embodiment is used for detecting the illumination light with a wavelength in the near-infrared region. Furthermore, in this imaging optical system 120, an imaging device 12 for detecting the illumination light with wavelength in the visible region is provided separately. In addition, in this imaging optical system 120, it can guide the signal light from the OCT unit 150 to the fundus oculi Ef and the signal light through the fundus oculi Ef to the OCT unit 150.

Also, the illuminating optical system 100 is comprised as in conventional ones including: an observation light source 101, a condenser lens 102, an imaging light source 103, a condenser lens 104, an exciter filter 105 and 106, a ring transparent plate 107, a mirror 108, an LCD 109, an illumination diaphragm 110, a relay lens 111, an aperture mirror 112, and an objective lens 113.

An observation light source 101 outputs the illumination light of a wavelength in the visible region included within about 400 nm to 700 nm. Furthermore, an imaging light source 103 outputs the illumination light of a wavelength in the near-infrared region included within about 700 nm to 800 nm. The near-infrared light output from this imaging light source 103 is provided shorter than the wavelength of the light used by the OCT unit 150 (to be described later).

At the same time, the imaging optical system 120 comprises: an objective lens 113, an aperture mirror 112 (aperture part 112a thereof), an imaging diaphragm 121, a barrier filter 122 and 123, a variable magnifying lens 124, a relay lens 125, an imaging lens 126, a dichroic mirror 134, a field lens (eye vision lens) 128, a half mirror 135, a relay lens 131, a dichroic mirror 136, an imaging lens 133, an imaging device 10 (an image pick-up element 10a), a reflection mirror 137, an imaging lens 138, an imaging device 12 (an image pick-up element 12a), and a lens 139 and LCD (Liquid crystal Display) 140.

The imaging optical system 120 related to the present embodiment is different from the conventional imaging optical system 120 shown in FIG. 11 in that a dichroic mirror 134, a half mirror 135, a dichroic mirror 136, a reflection mirror 137, an imaging lens 138, and a lens 139 and LCD 140 are provided.

The dichroic mirror 134 reflects the fundus reflection light of the illumination light from the illuminating optical system 100 (with a wavelength included within about 400 nm to 800 nm), and transmits the signal light LS (with a wavelength included within about 800 nm to 900 nm; to be described later) from the OCT unit 150. This dichroic mirror 134 is the equivalent of one example of the "optical combination and separation means" of the present invention.

Furthermore, the dichroic mirror 136 transmits the illumination light with a wavelength in the visible region from the illuminating optical system 100 (the visible light of a wavelength within about 400 nm to 700 nm for outputting from the observation optical source 101), and refrects the illumination light with a wavelength in the near-infrared region (the near-infrared light of a wavelength within about 700 nm to 800 nm for outputting from the imaging light source 103).

The LCD 140 shows an internal fixation target, etc. The light from this LCD 140 is reflected by the half mirror 135 after being converged by the lens 139, and reflects the dichroic mirror 136 through the field lens 128. Further, it enters the eye to be examined E passing through the imaging lens 126, the relay lens 125, the variable magnifying lens 124, the aperture mirror 112 (aperture part 112a thereof), the objective lens 113, etc. As a result, an internal fixation target, etc. is displayed in a fundus oculi Ef of an eye to be examined E.

The image pick up element 10a is the image pick up element of CCD and CMOS, etc. installed internally in an imaging device 10 such as a TV camera, and is particularly used for detecting light of a wavelength in the near-infrared region (that is, the imaging device 10 is the infrared TV camera for detecting near-infrared light). The imaging device 10 outputs the image signal as a result of detecting near-infrared light. A touch panel monitor 11 displays a 2-dimensional image (fundus image Ef') of the surface of the fundus oculi Ef based on this image signal. Also, this image signal is sent to the arithmetic and control unit 200, and the fundus oculi image is displayed on the display (to be described later). Furthermore, when the fundus oculi are being imaged by this imaging device 10, the illumination light output from the imaging light source 103 of the illuminating optical system 100, having a wavelength in the near-infrared region, is used.

Also, The image pick up element 12a is the image pick up element of CCD and CMOS, etc. installed internally in an imaging device 12 such as a TV camera, and is particularly used for detecting light of a wavelength in the visible region (that is, the imaging device 12 is the TV camera for detecting visible light). The imaging device 12 outputs the image signal as a result of detecting visible light. A touch panel monitor 11 displays a 2-dimensional image (fundus image Ef') of the surface of the fundus oculi Ef based on this image signal. Also, this image signal is sent to the arithmetic and control unit 200, and the fundus oculi image is displayed on the display (to be described later). Furthermore, when the fundus oculi are being imaged by this imaging device 12, the illumination light output from the observation light source 101 of the illuminating optical system 100, having a wavelength in the near-infrared region, is used.

Furthermore, the imaging optical system 120 of the present embodiment is provided with a scanning unit 141 and a lens 142. The scanning unit 141 is equipped with a constitution to scan the light output (signal light LS; to be described later) from the OCT unit 150 on a fundus oculi Ef.

The lens 142 incidents the signal light LS from the OCT unit 150 in the form of parallel light flux onto the scanning unit 141. Furthermore, the lens 142 acts so as to converge the fundus reflection light of the signal light LS that has reached through the scanning unit 141.

In FIG. 2, one example of a concrete composition of the scanning unit 141 is shown. The scanning unit 141 is comprised including Galvanometer mirrors 141A, 141B, and reflection mirrors 141C, 141D.

The Galvanometer mirrors 141A and 141B are to be rotatable centering around rotary shafts 141a and 141b respectively. The rotary shaft 141a and 141b are arranged perpendicular to each other.

In FIG. 2, the rotary shaft 141a of the Galvanometer mirror 141A is arranged parallel to the paper face on the same figure, while the rotary shaft 141b of the Galvanometer mirror 141B is arranged perpendicular to the paper face in the same figure. That is, the Galvanometer mirror 141B is to be rotatable in the directions indicated by an arrow pointing in both directions in FIG. 2, while the Galvanometer mirror 141A is to be rotatable in the directions perpendicular to the arrow pointing in both directions. As a result, this pair of Galvanometer mirrors 141A and 141B act so that the reflecting direction of the signal light LS changes to a direction perpendicular to each other.

Furthermore, the rotary movement of the Galvanometer mirror 141A and 141B respectively is driven by a drive mechanism containing drive device such as motor (see the mirror drive mechanism 241 and 242 shown in FIG. 5; to be described later). Galvanometer mirror 141A and 141B, and mirror drive mechanism 241 and 242 are a configuration of one example of the "scanning means".

The signal light LS reflected by the Galvanometer mirrors 141A and 141B is to be reflected by reflection mirrors 141C and 141D, and is to advance in the same direction as having entered into the Galvanometer mirror 141A.

As described previously, a conductive optical fiber 152a runs inside the connection line 152, and the end face 152b of the optical fiber 152a is arranged opposing the lens 142. The signal light LS emitted from this end face 152b advances while gradually expanding its beam diameter toward the lens 142 until being converged to a parallel light flux by this lens 142. On the contrary, the fundus reflection light of the signal light LS is converged toward the end face 152b by this lens 142.

Constitution of OCT Unit

Next, referring to FIG. 3, the constitution of an OCT unit 150 is described. The OCT unit 150 shown in the same figure has substantially the same optical system as a conventional optical image measuring device, and is equipped with an interferometer that splits the light output from a light source into reference light and signal light, and generates interference light by the reference light that has passed through a reference object and the signal light that has passed through an object to be measured (fundus oculi Ef), and at the same time, is configured to form images such as tomographic images and a 3-dimensional images of the fundus oculi Ef by analyzing the detection result of this interference light.

A low coherence light source 160 is composed of a broad band light source such as super luminescent diode (SLD) that outputs low coherence light L0 or a light emitting diode (LED), etc. This low coherence light L0, for instance, has a wave length in the near-infrared region and is supposed to be light having a time wise coherence length of approximately several tens of micro-meters. The low coherence light L0 output from the low coherence light source 160 has a longer wavelength than the illumination light (wavelength: about 400 nm to 800 nm) of the fundus camera unit 1A, for example, a wavelength included within about 800 nm to 900 nm. This low coherence light source 160 corresponds to an example of the "light source" of the present invention.

The low coherence light L0 output from the low coherence light source 160 is guided to an optical coupler 162 through an optical fiber 161 composed of, e.g. a single mode fiber, or PM (Polarization maintaining) fiber, and then split into reference light LR and signal light LS.

Furthermore, the optical coupler 162 has both actions, i.e. a means for splitting the light (splitter), and a means for overlaying the light (coupler); however, herein conventionally referred to as an "optical coupler".

The reference light LR generated by the optical coupler 162 is guided by an optical fiber 163 consisting of such as a single mode fiber, and emitted from the end face of the fiber. The emitted reference light LR is reflected by a reference mirror 174 (reference object) through a glass block 172 and a density filter 173 after having been converged into a parallel light flux by a collimator lens 171.

The reference light LR reflected by the reference mirror 174 is converged to the end face of the fiber of the optical fiber 163 by the collimator lens 171 again through the density filter 173 and the glass block 172. The converged reference light LR is guided to the optical coupler 162 through the optical fiber 163.

Furthermore, the glass block 172 and the density filter 173 act as a delaying means to match the optical path length (optical distance) between the reference light LR and the signal light LS, and as a means to match the dispersion characteristics of reference light LR and the signal light LS.

Furthermore, the reference mirror 174 is provided to be movable in the traveling direction of the reference light LR (the direction of the both-sided arrow shown in FIG. 3). As a result, it ensures the light path length of the reference light LR according to the length of the eyeball, etc. of an eye to be examined E. Moreover, shifting of the reference mirror 174 is operated to move by a drive mechanism including a motor, etc (reference mirror drive mechanism 243 shown in FIG. 5; to be described later).

Whereas, the signal light LS generated by the optical coupler 162 is guided to the end part of the connection line 152 by an optical fiber 164 consisting of such as a single mode fiber. A conductive optical fiber 152a runs inside the connection line 152. Herein, the optical fiber 164 and the optical fiber 152a may be composed of a single optical fiber, or may be jointly formed by connecting each end. In either case, it is sufficient as long as the optical fiber 164 and 152a are composed so as to be capable of transferring the signal light LS between the fundus camera unit 1A and the OCT unit 150.

The signal light LS is guided within the connection line 152 to the fundus camera unit 1A. Then, the signal light LS enters into the eye to be examined E through the lens 142, the scanning unit 141, the dichroic mirror 134 the imaging lens 126, the relay lens 125, the variable magnifying lens 124, the imaging diaphragm 121, the aperture part 112a of an aperture mirror 112, and the objective lens 113 (then, as described later, the barrier filter 122 and 123 as well as the quick return mirror 127 are retracted from the optical path respectively).

The signal light LS that has entered into the eye to be examined E forms an image on a fundus oculi (retina) Ef and is then reflected. Then, the signal light LS is not only reflected on the surface of the fundus oculi Ef, but is also scattered at the refractive index boundary reaching the deep area region of the fundus oculi Ef. As a result, the signal light LS passed through the fundus Ef becomes a light containing the information reflecting the surface state of the fundus oculi Ef and the information reflecting the scattered state in the rear at the refractive index boundary of the deep area tissue. The light is simply referred as "fundus reflection light (signal light LS thereof).

The fundus reflection light of the signal light LS advances reversely on the above route and converges at the end face 152b of the optical fiber 152a, then enters into the OCT unit 150 through this optical fiber 152, and returns to the optical coupler 162 through the optical fiber 164. The optical coupler 162 overlays this signal light LS and the reference light LR reflected at the reference mirror 174 to generate interference light LC. The generated interference light LC is guided into a spectrometer 180 through an optical fiber 165 consisting of such as a single mode fiber.

Herein, the "interference light generating means" in the present invention is comprised of an interferometer including at least an optical coupler 162, an optical fiber 163 and 164, and a reference mirror 174. Furthermore, although a Michelson type interferometer has been adopted in the present embodiment, for instance, a Mach Zender type, etc. or any optional type of interferometer may be adopted appropriately.

The spectrometer 180 is comprised of a collimator lens 181, a diffraction grating 182, an image forming lens 183, and a CCD (Charge Coupled Device) 184. The diffraction grating 182 in the present embodiment is a transmission type diffraction grating; however, needless to say, a reflection type diffraction grating may also be used. Furthermore, needless to say, in place of CCD 184, it is also possible to adopt other photo-detecting elements. This photo-detecting element is the equivalent of one example of the "detecting means" of the present invention.

The interference light LC made incident onto the spectrometer 180 is to be split (spectral resolution) by the diffraction grating 182 after having been converged into a parallel light flux by the collimator lens. The split interference light LC forms an image on the image pick up surface of the CCD 184 by the image forming lens 183. The CCD 184 receives this interference light LC that is to be converted to an electrical detection signal, and outputs this detection signal to the arithmetic and control unit 200.

Constitution of Arithmetic and Control Unit

Next, the configuration of the arithmetic and control unit 200 is described. This arithmetic and control unit 200 analyzes the detection signal input from the CCD 184 of the spectrometer 180 of the OCT unit 150, and performs a process of forming tomographic images of a fundus oculi Ef of an eye to be examined E. The analysis technique then is the same technique as the conventional Fourier domain OCT technique. Furthermore, the arithmetic and control unit 200 executes the control of each part of the fundus camera unit 1A and the control of each part of the OCT unit 150.

Also, the arithmetic and control unit 200 operates the treatment of forming a 2-dimensional image showing the state of the surface of a fundus oculi Ef (retina) based on the image signal output from the imaging device 10 and 12 of the fundus camera unit 1A.

Furthermore, the arithmetic and control unit 200 executes the control of each part of the fundus camera unit 1A and the control of each part of the OCT unit 150.

As for the control of the fundus camera unit 1A, to be controlled is, for example: controlling the output of illumination light by the observation light source 101 or the imaging light source 103; controlling the insertion/retraction operation of the exciter filters 105, 106, or the barrier filters 122, 123 on the optical path; controlling the display operation of the liquid crystal display 109; controlling the shift of the illumination diaphragm 110 (controlling the diaphragm value); controlling the diaphragm value of the imaging diaphragm 121; controlling the shift of the variable magnifying lens 124 (controlling the magnification), etc. Furthermore, the arithmetic and control unit 200 performs a control of rotary operations of the Galvanometer mirrors 141A, 141B within the scanning unit 141.

Whereas, as for the control of the OCT unit 150, output control of the low coherence light by a low coherence light source 160, control of accumulated time of the CCD 184, or movement control of reference mirror 174, etc. are to be performed.

The hardware configuration of the arithmetic and control unit 200 that acts as described above is explained referring to FIG. 4. The arithmetic and control unit 200 is provided with a hardware configuration that is the same as conventional computers. To be specific, the configuration includes: a microprocessor 201 (CPU, MPU, etc.), a RAM202, a ROM203, a hard disk drive (HDD) 204, a key board 205, a mouse 206, a display 207, an image forming board 208, and a communication interface (I/F) 209. Each part of these is connected through a bus 200a.

The microprocessor 201 executes operations characteristic to the present invention by rolling out a control program 204a that has been stored in the hard disk drive 204, on the RAM 202.

Furthermore, the microprocessor 201 executes control of each part of the devices that have previously been described and various arithmetic processes, etc. Moreover, control of each part of the devices that respond to an operation signal from the key board 205 or the mouse 206, control of display processes by the display 207, and control of transmitting/receiving processes of various types of data or control signals, etc. are executed by the communication interface 209.

The hard disk drive 204 stores various information such as patient information, including patient names and patient IDs, and image data, including fundus image. The patient information stores information that shows the reference mirror 174 position (position information of the reference mirror) at the time the fundus image was measured by the OCT unit 150 and information that shows such scanning positions as the scanning start position, the scanning end position, and the scanning interval (scanning position information).

The reference mirror position information is, for example, information that shows the position of the reference mirror 174 corresponding to the position at which brightness value reaches a specific signature value in the depth direction of the tomographic images of the fundus oculi Ef (z direction in FIG. 1). For the specific signature value, for example, the position at which brightness value reaches a maximum level in the depth direction of the tomographic images (position at which the detected intensity of the interface light reaches maximum) can be used. The reference mirror 174 position corresponding to the position at which brightness reaches maximum can be obtained by analyzing the tomographic images, for example. The position at which brightness reaches maximum is the retinal pigment epithelium of an eye to be examined E, for example.

The specific signature value is not limited to the maximum brightness value, so any value can be used, as long as it is specifiable by analyzing tomographic images such as the minimum value, the local maximal value, and the local minimal value. For example, if tomographic images have a black background (minimum brightness), the position at which brightness reaches maximum (the brightest position in the tomographic images) and the position at which brightness reaches the local maximal value (the brightest position in a specific region of the tomographic images), etc., can be used as the aforementioned signature value. Furthermore, if tomographic images have a white background (minimum brightness), the position at which brightness reaches minimum (the darkest position in the tomographic images) and the position at which brightness reaches the local minimal value (the darkest position in the specific region of the tomographic images), etc., can be used as the above signature value.

The key board 205, the mouse 206 and the display 207 are used as a user interface of the fundus observation device 1. The key board 205 is used as a device for entering letters or figures, etc. by typing. The mouse 206 is used as a device to perform various entry operations with respect to the display screen of the display 207. The key board 205, the mouse 206 are used as an example of the "input means" of the present invention.

Furthermore, the display 207 being an optional display device such as LCD (Liquid Crystal Display) or CRT (Cathode Ray Tube), etc. displays images of a fundus oculi Ef formed by the fundus observation device 1 and displays various operation screens or set up screens, etc.

Furthermore, the user interface of the fundus observation device 1 is not limited to such a configuration but may be configured by using an optional user interface means equipped with a function to display and output various information such as track ball, joystick, touch panel type LCD, control panel for ophthalmology examinations, and with a function to input various information.

An image forming board 208 is a dedicated electronic circuit for operating to form the image of the fundus oculi Ef of an eye to be examined E. In this image forming board 208, the fundus image forming board 208a and OCT image forming board 208b are installed. The fundus image forming board 208a is a dedicated electronic circuit for operating in order to form the image of the fundus oculi based on the image signal from the imaging device 10 and the imaging device 12 of the fundus camera unit 1A. Furthermore, the OCT image forming board 208b is a dedicated electronic circuit for operating in order to form fundus images (tomographic images) based on the detecting signal from CCD 184 of the spectrometer 180 in the OCT unit 150. The image forming board 208 allows the processing speed for forming fundus images to improve.

A communication interface 209 operates to send the various control signal from a microprocessor 201 to the fundus camera unit 1A and OCT unit 150. Also, the communication interface 209 operates to receive the image signal from the imaging device 10 and 12 in the fundus camera unit 1A and the detecting signal from CCD 184 in the OCT unit 150, and it operates to input the image forming board 208. At this time, the communication interface 209 operates to input the image signal from the imaging device 10 and 12 to the fundus image forming board 208a, and it operates to input the detecting signal from CCD 184 to OCT image forming board 208b.

Moreover, when the arithmetic and control unit 200 is connected to a network such as LAN (Local Area Network) or Internet, etc., the communication interface 209 may be configured to be equipped with a network adopter such as LAN card, etc. or a communication equipment such as modem, etc. so as to be able to perform data communication through the network. In this case, a server accommodating the control program 204a may be installed, and at the same time, the arithmetic and control unit 200 may be configured as a client terminal of the server.

Furthermore, servers and databases on the network can be configured to store any of the various information (mentioned above) stored on a hard disk drive 204.

Control System Configuration

The configuration of the control system of the fundus observation device 1 having the configuration described above is explained referring to FIG. 5. FIG. 5 shows a part related to the operations or processes of the present embodiment that has been particularly selected from among constituents composing the fundus observation device 1.

The control system of the fundus observation device 1 is configured mainly having a controlling part 210 of the arithmetic and control unit 200. The controlling part 210 is comprised including: the microprocessor 201, the RAM202, the ROM203, the hard disk drive 204 (control program 204a), and the communication interface 209.

The controlling part 210 executes said controlling processes by the microprocessor 201 that is operated based on the control program 204a. Particularly, by controlling the mirror drive mechanisms 241, 242 of the fundus camera unit 1A respectively, the Galvanometer mirrors 141A, 141B respectively may be operated independently.

Furthermore, the controlling part 210 executes control for displaying two kinds of images produced by the fundus observation device 1: that is, a 2-dimensional image (fundus image Ef) of the surface of a fundus oculi Ef by the fundus camera unit 1A, and an image of a fundus oculi Ef formed based on the detection signal obtained by the OCT unit 150, parallel to each other on the display 207 of the user interface 240. These fundus images are simultaneously displayed on the display 207 respectively.

An image forming part 220 is intended to operate the process forming the fundus image based on the image signal from the imaging device 10 and 12 of the fundus camera unit 1A and the process forming the fundus image based on the detecting signal from CCD 184 in the OCT unit 150 including the image forming board 208.

The image processing part 230 is used for various image processes to the fundus images formed by the image forming part 220. For example, it operates to form a 3-dimensional image of the fundus oculi Ef based on the tomographic images of the fundus oculi Ef corresponding to the detection signal from the OCT unit 150 and executes various corrections, such as brightness adjustment.

The information storage part 225 stores the reference mirror position information that shows the position of the reference mirror 174 when the fundus image was observed by the OCT unit 150 and the scanning position information of the signal light LS that shows the scanning start position, the scanning end position, and the scanning interval. The reference mirror position information and the scanning position information are stored in relation to the identification information that identifies an eye to be examined where the fundus image was observed. For identification information, the patient ID of said patient can be used. The information storage part 225 is configured to include a hard disk drive 204 and works as one of the "storing means" of the present invention.

The search processing part 235 performs searches in the information storage part 225 for the reference mirror position information and/or the scanning position information associated with identification information that is input using a keyboard 205 and mouse 206. The search processing part 235 is configured to include a microprocessor 201 and works as one of the "searching means" of the present invention.

The user interface (UI) 240 is equipped with input devices (operation devices) such as a keyboard 205 and mouse 206 and with display devices such as the display 207. The keyboard 205 and mouse 206 are used to input the identification information (patient ID, etc.) of an eye to be examined (patient), as mentioned above.

The controlling feature of the scanning signal light LS by the controlling part 210 and the process feature to the detecting signal from the OCT unit 150 by the image forming part 220 and the image processing part 230 are respectively described below. Furthermore, an explanation regarding the process of the image forming part 220, etc., to the image signal from the fundus camera unit 1A is omitted because it is the same as the conventional process.

Regarding the Signal Light Scanning

Scanning of signal light LS is performed by changing the facing direction of the reflecting surfaces of the Galvanometer mirrors 141A and 141B of the scanning unit 141 in the fundus camera unit 1A. By controlling the mirror drive mechanisms 241 and 242 respectively, the controlling part 210 changes the facing direction of the reflecting surfaces of the Galvanometer mirror 141A and 141B, and scans the signal light LS on the fundus oculi Ef.

Once the facing direction of the reflecting surface of the Galvanometer mirror 141A is changed, the signal light LS is scanned in a horizontal direction (x-direction in FIG. 1) on the fundus oculi Ef. Whereas, once the facing direction of the reflecting surface of the Galvanometer mirror 141A is changed, the signal light LS is scanned in a vertical direction (y-direction in FIG. 1) on the fundus oculi Ef. Furthermore, by changing the facing direction of the reflecting surfaces of both Galvanometer mirrors 141A and 141B simultaneously, the signal light LS may be scanned in the combined x-direction and y-direction. That is, by controlling these two Galvanometer mirrors 141A and 141B, the signal light LS may be scanned in an arbitrarily direction on the xy plane.

FIG. 6 represents one example of scanning features of signal light LS for forming images of a fundus oculi Ef. FIG. 6(A) represents one example of scanning features of the signal light LS, when the signal light LS sees the fundus oculi Ef from an incident direction onto the eye to be examined E (that is, +direction of z is seen from direction of z in FIG. 1). Furthermore, FIG. 6(B) represents one example of arrangement features of scanning points (positions at which image measurement is carried out) on each scanning line on the fundus oculi Ef.

As shown in FIG. 6(A), the signal light LS is scanned within a rectangular shaped scanning region R that has been preset. Within this scanning region R, plural (m number of) scanning lines R1 through Rm have been set in the x-direction. When the signal light LS is scanned along each scanning line Ri (i=1 through m), detection signals of interference light LC are to be generated.

Herein, the direction of each scanning line Ri is referred as the "main scanning direction" and the orthogonally crossing direction is referred as the "sub-scanning direction". Therefore, the scanning of the signal light LS in a main scanning direction is performed by changing the facing direction of the reflecting surface of the Galvanometer mirror 141A, and the scanning in a sub-scanning direction is performed by changing the facing direction of the reflecting surface of the Galvanometer mirror 141B.

On each scanning line Ri, is shown in FIG. 6(B), a plurality (n number of) of scanning points Ri1 through Rin have been preset.

In order to execute the scanning shown in FIG. 6, the controlling part 210 controls the Galvanometer mirrors 141A and 141B to set the incident target of the signal light LS with respect to a fundus oculi Ef at a scan start position RS (scanning point R11) on the first scanning line R1. Subsequently, the controlling part 210 controls the low coherence light source 160 to flush the low coherence light L0 for emitting the signal light LS to the scan start position RS. The CCD 184 receives the interference light LC based on the fundus reflection light of this signal light LS at the scan start position RS, and outputs detection signals to the controlling part 210.

Next, by controlling the Galvanometer mirror 141A the controlling part 210 scans the signal light LS in a main scanning direction and sets the incident target at a scanning point R12, triggering a flush emission of the low coherence light L0 for making the signal light LS incident onto the scanning point R12. The CCD 184 receives the interference light LC based on the fundus reflection light of this signal light LS at the scanning point R12, and then outputs the detection signal to the controlling part 210.

Likewise, the controlling part 210 obtains detection signals output from the CCD 184 responding to the interference light LC with respect to each scanning point, by flush emitting the low coherence light L0 at each scanning point while shifting the incident target of the signal light LS from scanning point R13, R14, - - -, R1 (n−1), R1n in order.

Once the measurement at the last scanning point R1n of the first scanning line R1 is finished, the controlling part 210 controls the Galvanometer mirrors 141A and 141B simultaneously and shifts the incident target of the signal light LS to the first scanning point R21 of the second scanning line R2 following a line switching scan r. Then, by conducting the previously described measurement with regard to each scanning point R2j (j=1 through n) of this second scanning line R2, a detection signal corresponding to each scanning point R2j is obtained.

Likewise, by conducting a measurement with respect to the third scanning line R3, - - -, the m−1th scanning line R (m−1), the mth scanning line Rm respectively to obtain the detection signals corresponding to each scanning point. Furthermore, the symbol RE on a scanning line Rm is a scan end position in accordance with a scanning point Rmn.

As a result, the controlling part 210 obtains m×n number of detection signals corresponding to m×n number of scanning points Rij (i=1 through m, j=1 through n) within the scanning region R. Hereinafter, a detection signal corresponding to the scanning point Rij may be represented as Dij.

Such interlocking control of such shifting of scanning points and the output of the low coherence light L0 may be realized by synchronizing, for instance, the transmitting timing of control signals with respect to the mirror drive mechanisms 241, 242 and the transmitting timing of control signals (output request signal) with respect to the low coherence light source 160.

As described, when each Galvanometer mirror 141A and 141B is being operated, the controlling part 210 stores, in the information storage part 225, the position of each scanning line Ri or the position of each scanning point Rij (coordinate on the xy coordinate system) as information indicating the content of the operation. This stored content (scan positional information) is used in an image forming process as was conducted conventionally.

Regarding Image Processing

Next, one example of the process relating to OCT images is described of the image forming part 220 and the image processing part 230.

The image forming part 220 executes the formation process of tomographic images of a fundus oculi Ef along each scanning line Ri (main scanning direction). The image processing part 230 executes the formation process of a 3-dimensional image of the fundus oculi Ef based on these tomographic images formed by the image forming part 220.

The formation process of a tomographic image by the image forming part 220, as was conventionally done, includes a 2-step arithmetic process. In the first step of the arithmetic process, based on a detection signal Dij corresponding to each scanning point Rij, an image in the depth-wise direction (z-direction in FIG. 1) of a fundus oculi Ef at the scanning point Rij is formed.

Figure 7:
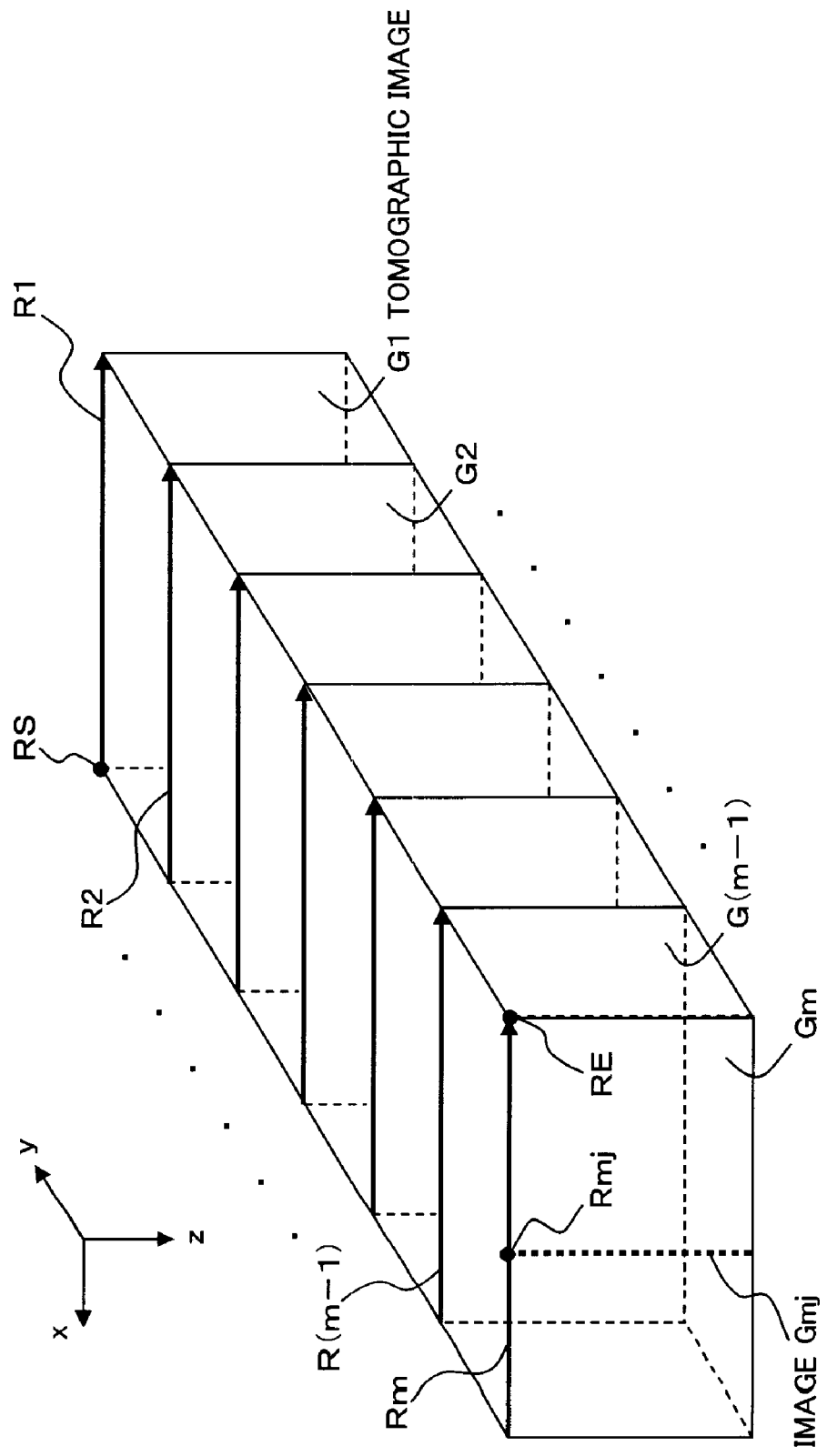
FIG. 7 is a schematic diagram representing one example of the scanning features of signal light and tomographic image features formed along each scanning line in a favorable embodiment of the fundus observation device configured to include the optical image-measuring device related to the present invention.

FIG. 7 represents a feature of a tomographic image formed by the image forming part 220. In the second step of the arithmetic process, with regard to each scanning line Ri, based on the images in the depth-wise direction at the n number of scanning points Ri1 through Rin thereon, a tomographic image Gi of a fundus oculi Ef along this scanning line Ri is formed. Then, the image forming part 220 determines the arrangement and the distance of each scanning point Ri1 through Rin while referring to the positional information (said scan positional information) of each scanning point Ri1 through Rin, and forms this scanning line Ri. Due to the above process, m number of tomographic images G1 through Gm at different positions of the sub-scanning direction (y-direction) are obtained.

Next, the formation process of a 3-dimensional image of a fundus oculi Ef by the image processing part 230 is explained. A 3-dimensional image of a fundus oculi Ef is formed based on the m number of tomographic images obtained by the above arithmetic process. The image processing part 230 forms a 3-dimensional image of the fundus oculi Ef by performing a publicly known interpolating process to interpolate an image between the adjacent tomographic images Gi and G (i+1).

Then, the image processing part 230 determines the arrangement and the distance of each scanning line Ri while referring to the positional information of each scanning line Ri to form this 3-dimensional image. For this 3-dimensional image, a 3-dimensional coordinate system (x,y,z) is set up, based on the positional information (said scan positional information) of each scanning point Rij and the z coordinate in the images of the depth-wise direction.

Furthermore, based on this 3-dimensional image, the image processing part 230 is capable of forming a tomographic image of the fundus oculi Ef at a cross-section in an arbitrary direction other than the main scanning direction (x-direction). Once the cross-section is designated, the image processing part 230 determines the position of each scanning point (and/or an image in the depth-wise direction that has been interpolated) on this designated cross-section, and extracts an image (and/or image in the depth-wise direction that has been interpolated) in the depth-wise direction at each determined position to form a tomographic image of the fundus oculi Ef at the designated cross-section by arranging plural extracted images in the depth-wise direction.

Furthermore, the image Gmj in FIG. 7 represents an image in the depth-wise direction (z-direction) at the scanning point Rmj on the scanning line Rm. Likewise, an image in the depth-wise direction at each scanning point Rij on the scanning line Ri formed by the arithmetic process of said first step may be represented as "image Gij."

Operation

Figure 8:
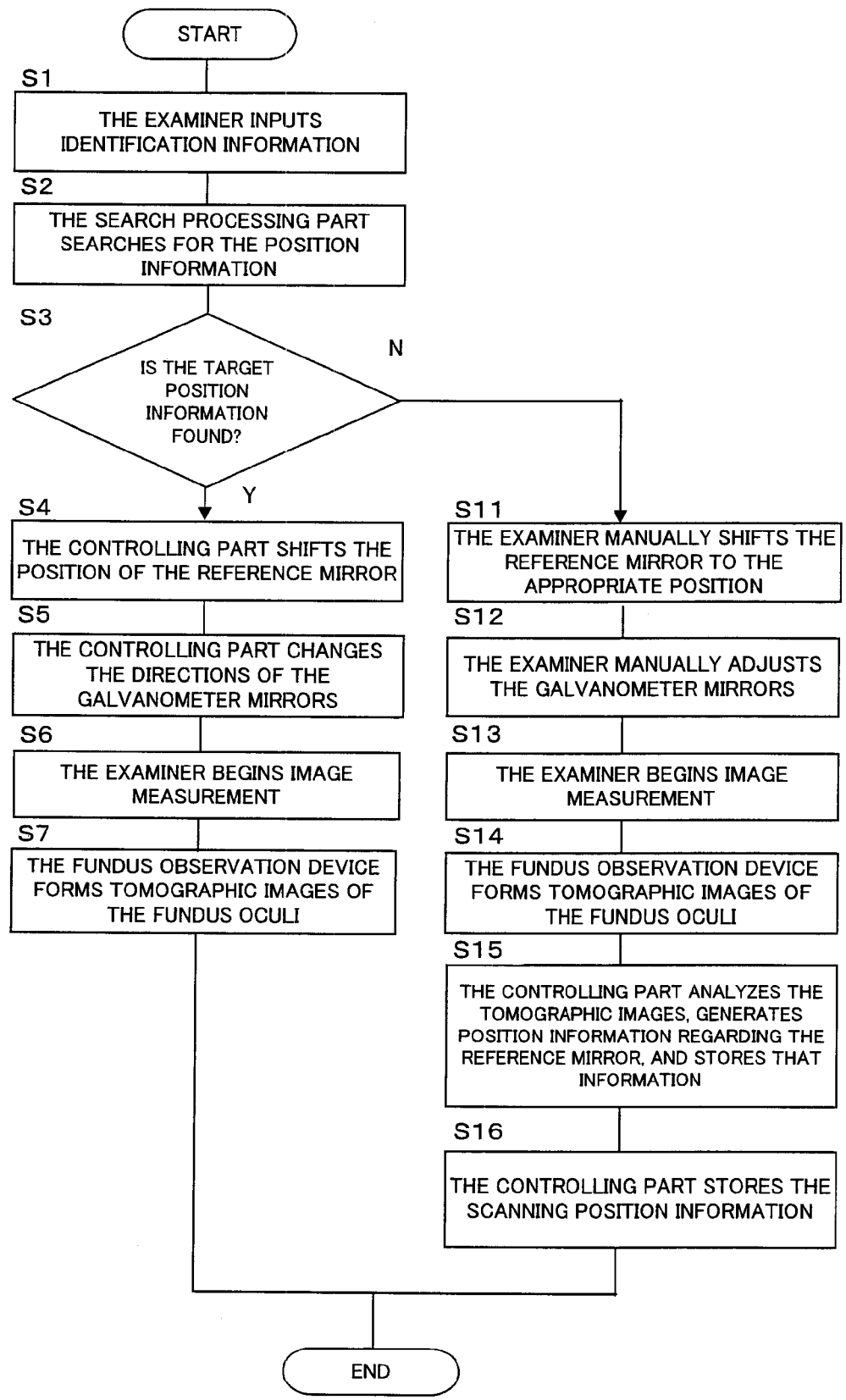
FIG. 8 is a flow chart that shows an example of the operation of the preferred embodiment of the fundus observation device configured to include the optical image-measuring device related to the present invention.

The operation of the fundus observation device 1 that has a configuration as described above is explained. Herein, image measurement of the fundus oculi Ef using an OCT unit 150, which is characterized by the present invention, is explained with reference to FIG. 8. The flowchart shown in FIG. 8 shows one of the processing flows in image measurement using the OCT unit 150.

First, the examiner inputs identification information for the eye to be examined E (patient) using a keyboard 205 and mouse 206 (S1). The controlling part 210 sends identification information that has been input into the search processing part 235. The search processing part 235 searches for the position information of the reference mirror and the scanning position information that is associated with identification information in the search processing part 225 (S2).

When the Position Information is Found

When the target position information is found (S3; Y), the controlling part 210 controls the reference mirror drive mechanism 243 based on the position information of the reference mirror that is found and shifts the position of the reference mirror 174 (S4). Consequently, the reference mirror 174 is shifted to the position at which the image measurement was previously performed on said eye to be examined E.

Furthermore, the controlling part 210 controls both mirror drive mechanisms 241 and 242 based on scanning position information that is found, and changes the directions of the galvanometer mirrors 141A and 141B (S5). Consequently, the galvanometer mirrors 141A and 141B are shifted to a direction to radiate the signal light LS onto the scanning start position RS (refer to FIGS. 6 and 7) where image measurement was previously performed on said eye to be examined E. Because the scanning position information that is found is referenced in the scanning process of the signal light LS to be described later, the information is stored in RAM 202, for example.

Next, the examiner performs a specific operation to begin image measurement of the fundus oculi Ef (S6). An eye to be examined E is situated at a specific position for measurement in any one of the pre-steps of Steps S1 to S6 (In other words, the patient's chin is placed on the chin rest 6).

The fundus observation device 1, when requested to start the image measurement, forms tomographic images of the fundus oculi Ef while scanning the signal light LS in the aforementioned manner (S7). At this time, the signal light LS is scanned based on the scanning position information that is found. The tomographic images that are thus formed are stored in the information storage part 225. This completes the process for when position information is found.

When Position Information is Not Found

On the other hand, when position information is no found (S3; N), the examiner manually shifts the reference mirror 174 to the appropriate position (S11) and adjusts the galvanometer mirrors 141A and 141B toward the appropriate direction (S12), for example. At this time, the examiner sets the scanning end position and the scanning interval as needed.

The position of the reference mirror 174 in Step S11 is determine based on data regarding the length of the eyeball of an eye to be examined E, for example. Furthermore, the orientation of the galvanometer mirrors 141A and 141B is determined by checking the surgical area while observing the image of the fundus oculi Ef obtained by the fundus camera unit 1A.

Next, the examiner performs a specific operation to start image measurement of the fundus oculi Ef (S13). Following that operation, the fundus observation device 1 forms tomographic images on the fundus oculi Ef while scanning the signal light LS in the aforementioned manner (S14).

The controlling part 210 analyzes the tomographic images that are thus formed, generates position information regarding the reference mirror, and stores that information in the information storage part 225 with links to the identification information that is input in Step S1 (S15). Furthermore, the controlling part 210 stores the scanning start position, the scanning end position, and the scanning interval in Step S12 in the information storage part 225 as the scanning position information with links to the identification information (S16). This completes the process for when position information is not found.

Action and Effect

The action and effect of the fundus observation device 1 (optical image-measuring device) related to the present embodiment having the above configuration is explained.

According to the fundus observation device 1, the reference mirror 174 is automatically shifted to the position at which said fundus oculi was previously observed when repeatedly observing the fundus oculi of the same eye to be examined, which reduces the time required for the examination. Furthermore, the positioning task that had previously been done manually for the reference mirror 174 is no longer necessary, which reduces the troublesome tasks before starting the examination.

Furthermore, according to the fundus observation device 1, the directions of the galvanometer mirrors 141A and 141B can be automatically set to radiate the signal light LS onto the scanning start position in the fundus observation that was previously performed for said eye to be examined when repeatedly observing the fundus oculi of the same eye to be examined, which shortens the examination time. In addition, the setting task that had previously been done manually for the scanning start position of the signal light LS is no longer necessary, which reduces troublesome tasks before beginning an examination.

Furthermore, the device is configured to scan the signal light LS based on the scanning position information as the scanning end position and the scanning interval in the fundus observation, which shortens the examination time. Furthermore, the setting task that had previously been done manually for scanning the signal light LS is no longer necessary, which reduces some troublesome tasks before beginning an examination.

Furthermore, the fundus observation device 1 stores the position information of the reference mirror that shows the reference mirror 174 position and the scanning position information that shows the orientation of the galvanometer mirrors 141A and 141B (the scanning position of the signal light LS) with links to the identification information of the respective eye to be examined being used for the examination by the fundus observation device 1. Moreover, when identification information for a certain eye to be examined is input, the device searches for reference mirror position information and scanning position information associated with the identification information and automatically sets the position of the reference mirror 174 and the orientation of the galvanometer mirrors 141A and 141B. Consequently, the position of the reference mirror 171 and the orientation of the galvanometer mirrors 141A and 141B can be set appropriately for each eye to be examined.

MODIFIED EXAMPLE

The configuration described above is merely one example to preferably implement the optical image-measuring device related to the present invention. Therefore, optional modifications may be implemented appropriately within the scope of the present invention. The various modified examples of the optical image-measuring device related to the present invention are explained hereafter.

In the above embodiment, the examiner manually inputs the identification information of the eye to be examined, bit may enter the identification information by reading recording media containing the information (patient ID card, etc.), for example. Recording media with any recording method for recording the identification information magnetically, onto IC chips, onto barcodes, etc. can be used. Moreover, in this case, a reading device (reader) for reading the information that is recorded on said recording media is used as an "input means" for the present invention.

Moreover, in the above embodiment, the forming process of the fundus image by the image forming part 220 (image forming board 208) and each controlling process are operated by the control part 210 (microprocessor 201, etc.), but it can be composed to operate these two processes by one or several computers.

In addition, the scanning position information may be set, based on the coordinates (xy coordinates shown in FIGS. 1, 6, and 7) of the signature areas in the fundus image Ef. An example of such setting methods of the scanning position information is shown in FIG. 9. To set the scanning start position RS and the scanning end position RE in the scanning region R for examining the state of the focused area Q (surgical area, treated area, affected area, etc.), first obtain the xy coordinates in the position P0 of the optic papilla in the fundus image Ef. Then, for the signature area close to the focused area Q, obtain the xy coordinates in the position P1 of the branching area of the fundus vessel. At that time, obtain the relative coordinates in the position P1 of the branching area to the position P0 of the optic papilla. Moreover, obtain the xy coordinates in the scanning start position RS as the relative coordinates for the position P1 of the branching area. In addition, obtain the xy coordinates in the scanning end position RE as the relative coordinates for the scanning start position RS.

Furthermore, in the above embodiment, the information showing the reference mirror 174 position at which brightness value reaches a specific signature value in the depth direction of the tomographic images of the fundus oculi Ef (the position of retinal pigment epithelium, for example) is used as the reference mirror position information, but the information is not limited to this. For example, if data regarding the length of the eyeball (eyeball length information) of said eye to be examined E is already obtained, accuracy of the reference mirror 174 positioning can be improved by determining and correcting the reference mirror position, based on the eyeball length information.

In the above embodiment, the fundus observation device that has functions of a fundus camera and of an optical image-measuring device was explained, but the configuration of the present invention can be applied to devices that have other fundus-observing functions, such as the functions of a slit-lamp microscope, for example, and the functions of an optical image-measuring device.

Furthermore, the configuration related to the present invention is applicable not only to such compound devices but also to single units of a normal optical image-measuring device.

For example, a configuration of the present invention that automatically sets the reference object position can be applied to any optical image-measuring devices that are configured to position the fundus oculi in a depth direction according to the reference object position such as that described in JP Patent Application No. 2005-337628 and JP Patent laid-open No. 2005-241464, both devised by the present inventors.

Furthermore, a configuration of the present invention that automatically sets the scanning position of the signal light can be applied to any optical image-measuring devices that have a configuration for scanning the signal light using galvanometer mirrors such as that described in JP Patent Application No. 2005-337628.

What is claimed is:

1. An optical image-measuring device having:
   a light source;
   an interference optical generator configured to split light that is emitted from said light source into a signal light directed toward a fundus oculi of an eye to be examined and a reference light directed toward a reference mirror, to generate an interference light by superimposing said signal light passed through said fundus oculi and said reference light reflected by said reference mirror;
   a detector configured to detect said interference light that is generated,
   an image generator configured to form tomographic images of said fundus oculi based on the detection results by said detector,
   wherein the optical image-measuring device comprises a storing part configured to store position information indicating a stationary position of said reference mirror based on previously formed said tomographic images; and
   a driving part configured to shift said reference mirror toward the optical path direction of said reference light to said stationary position of said reference mirror indicated by said position information related to said eye to be examined, which is stored in said storing part, wherein said driving part is configured to fix the position of said reference mirror after said reference mirror is moved to said stationary position indicated by said position information, and
   said image generator is configured to form said tomographic images of said fundus oculi for measurement depth of said fundus oculi determined from said stationary position of said reference mirror.

2. An optical image-measuring device according to claim 1, wherein:
   said storing part is configured to store said reference object position information at the time said tomographic images of said fundus oculi of an eye to be examined were formed, with links to identification information regarding said eye to be examined, the optical image-measuring device further comprising:
   an input part configured to input said identification information regarding said eye to be examined; and
   a searching part configured to search said position information linked to said identification information input from said storing part,
   wherein said drive part is configured to shift said reference object to a position indicated by said position information searched above.

3. An optical image-measuring device according to claim 1, wherein said reference object position information shows said reference object position corresponding to the position at which brightness reaches a specific signature value in the depth direction of previously formed said tomographic images.

4. An optical image-measuring device according to claim 1,
   wherein said storing part is further configured to store eye length information of an eye to be examined and
   said driving part is configured to shift said reference object toward the optical path direction of said reference light to a position determined from said reference object position information and said eye length information related to said eye to be examined being stored as above.

* * * * *